United States Patent
Rees et al.

(10) Patent No.: US 10,398,775 B2
(45) Date of Patent: Sep. 3, 2019

(54) STERILISATION OF S-NITROSOTHIOLS

(71) Applicant: Salupont Consulting Ltd., Sandy Bedfordshire (GB)

(72) Inventors: Daryl Rees, Sandy (GB); Antonia Orsi, Sandy (GB)

(73) Assignee: Salupont Consulting Ltd., Sandy Bedfordshire (GB)

( * ) Notice: Subject to any disclaimer, the term of this patent is extended or adjusted under 35 U.S.C. 154(b) by 0 days.

(21) Appl. No.: 15/561,196

(22) PCT Filed: Mar. 21, 2016

(86) PCT No.: PCT/GB2016/050772
§ 371 (c)(1),
(2) Date: Sep. 25, 2017

(87) PCT Pub. No.: WO2016/156794
PCT Pub. Date: Oct. 6, 2016

(65) Prior Publication Data
US 2018/0055932 A1 Mar. 1, 2018

(30) Foreign Application Priority Data
Mar. 27, 2015 (GB) .................................. 1505347.3

(51) Int. Cl.
| | |
|---|---|
| *A61L 2/00* | (2006.01) |
| *A61K 41/00* | (2006.01) |
| *A61K 38/05* | (2006.01) |
| *A61K 31/198* | (2006.01) |
| *A61P 1/00* | (2006.01) |

(52) U.S. Cl.
CPC ........ *A61K 41/0009* (2013.01); *A61K 31/198* (2013.01); *A61K 38/05* (2013.01); *A61K 41/0019* (2013.01); *A61L 2/007* (2013.01); *A61L 2/0029* (2013.01); *A61L 2/0035* (2013.01); *A61P 1/00* (2018.01); *A61L 2202/18* (2013.01); *A61L 2202/21* (2013.01)

(58) Field of Classification Search
None
See application file for complete search history.

(56) References Cited

U.S. PATENT DOCUMENTS

2010/0096287 A1* 4/2010 Stoesz ................ A61K 31/4375
206/438

FOREIGN PATENT DOCUMENTS

WO 2008153762 12/2008

OTHER PUBLICATIONS

Silindir et al., Sterilization Methods and the Comparison of E-Beam Sterilization with Gamma Radiation Sterilization, FABAD J. Pharm. Sci., 34, 43-53, 2009 (Year: 2009).*
International Search Report and Written Opinion in corresponding PCT/GB2016/050772, dated Jun. 20, 2016.
Lin, et al., "Identification of the nitrate produced from gamma-radiation sterilization of S-Nitrosoglutathione", American Chemical Society 230th National Meeting of the American-Chemical-Society, Washington, D.C., Aug. 28-Sep. 1, 2005, retrieved from: http://oasys2.confex.com/acs/230nm/techprogram/P885814.HTM.
International Preliminary Report on Patentability in corresponding PCT/GB2016/050772, dated Oct. 12, 2017.
Singh, et al., "Photosensitized decomposition of S-nitrosothiols and 2-methyl-2-nitrosopropane Possible use for site-directed nitric oxide production", FEBS Letters, vol. 360, 1995, pp. 47-51.
Stamler, et al., "The decomposition of thionitrites", Curr Opin Chem Biol., Dec. 2002, vol. 6, issue 6, pp. 779-785.
Veleeparampil, et al., "Decomposition of S-Nitrosothiols Induced by UV and Sunlight", Advances in Physical Chemistry, 2009, Article ID 890346, 5 pages.
Parent, et al., "A Complete Physicochemical Identity Card of S-nitrosoglutathione", Current Pharmaceutical Analysis 2013, vol. 9, pp. 31-42.
"The Science and Practice of Pharmacy", 21st ed., David Troy, 2006 (3 pages).
"Essentials of Pharmaceutics", Ed. Linda Felton, 2013 (66 pages).
"Sterility and Sterility Assurance", Pharmaceutical Microbiology, 2016 (14 pages).

* cited by examiner

*Primary Examiner* — Jennifer A Berrios
(74) *Attorney, Agent, or Firm* — Hovey Williams LLP (57) ABSTRACT

This invention provides a method of sterilizing an S-nitrosothiol, for example S-nitrosoglutathione, without reduction of purity by more than about 5.0% through degradation. The invention allows sterile S-nitrosothiol or a sterile pharmaceutical pre-composition comprising S-nitrosothiol, wherein the S-nitrosothiol is in dry solid form, to be produced. The sterile pharmaceutical pre-composition is mixed with one or more diluents, excipients, carriers, additional active agents, or any combination thereof, for example sterile saline, to prepare a pharmaceutical composition of S-nitrosothiol for use.

15 Claims, 3 Drawing Sheets

STERILISATION OF S-NITROSOTHIOLS

RELATED APPLICATIONS

This application is the National Stage of International Patent Application No. PCT/GB2016/050772, filed Mar. 21, 2016, which is hereby incorporated by reference in its entirety, and which claims priority to United Kingdom Patent Application No. 1505347.3, filed Mar. 27, 2015.

FIELD OF THE INVENTION

The present invention relates to sterile S-nitrosothiols and sterile pharmaceutical pre-compositions containing S-nitrosothiols, which can be made up into a sterile pharmaceutical composition with one or more sterile pharmaceutical diluents, excipients, carriers, additional active agents, or any combination thereof, as desired, for pharmaceutical or veterinary use. The present invention also relates to a process for the production of the sterile materials without substantial loss of S-nitrosothiol purity, and to kits and methods for preparing the ready-to-use pharmaceutical compositions.

BACKGROUND OF THE INVENTION

S-nitrosothiols, namely molecules having the basic structure R—S—N=O, where R is any organic group, e.g., S-nitrosoglutathione (GSNO), S—NO-cysteine (S—NO-Cys), S-nitroso-N-acetylpenicillamine (SNAP), and nitroso derivatives of proteins such as albumin and haemoglobin (Hb), for example SNO-albumin and poly-SNO-albumin, exert nitric oxide-like activity in vivo. They cause arterial and venous smooth muscle relaxation, inhibit platelet aggregation, and activate guanylate cyclase (Rees et al., 1989b; Rees et al., 1989a), (Rees et al., 2001), (Radomski et al., 1992). They are also involved, for example, in immunosuppression, neurotransmission, and host defence.

Vasoactive S-nitrosothiols are known to be generated in vivo (Keaney et al., 1993), (Stamler et al., 1992), (Al-Sa'doni et al., 2000). The total S-nitrosothiols in plasma has been reported to range from 40 nM to 7 µM in humans and rodents under non-inflammatory conditions (Stamler et al., 1992). S-nitrosothiol compounds can release nitric oxide when required via reactions with transition metal ions or other reducing agents. They are envisioned as a buffering system that controls intra- and extra-cellular activities of NO, and magnify the range of its action. Once formed, S-nitrosothiols can directly transfer the nitrosyl cation (NO$^+$) to another thiol via the so-called transnitrosation reaction, which ensures the dynamic state of S-nitrosothiols in vivo (Singh et al., 1996a; Singh et al., 1996b), (Butler et al., 1997).

S-nitrosoglutathione (GSNO)

is in clinical development as a pharmaceutical composition for human or veterinary therapy or prophylaxis.

S-nitrosothiols are sensitive to air, temperature, moisture and electromagnetic radiation, and require careful storage and handling to avoid degradation (Singh et al., 1995), (Stamler et al., 2002), (Manoj et al., 2009), (Parent et al., 2013). Nevertheless, even under strictly controlled air, radiation and temperature conditions, long term storage of S-nitrosothiols, as required for pharmaceutical products, results in degradation. For pharmaceutical use, this instability poses serious problems in terms of the purity of the active agent and compliance with pharmaceutical grade requirements, as well as accuracy and predictability of the dosing of the active agent. Upon storage under inert atmosphere (argon and nitrogen) at –20° C. and in the dark, S-nitrosoglutathione, stored as a solid, has only been reported to be stable for 6 months (Parent et al., 2013). Upon storage under further controlled air, radiation and temperature conditions, S-nitrosoglutathione, prepared by a specific method said to impart stability in solid form, has only been reported to be stable for 9 months (Looker et al., 2008); (WO 2008/153762, Example 3 of the reference).

Liquid formulations of S-nitrosothiols are even more unstable and decompose quantitatively in hours, such that only about 85% of the initial S-nitrosoglutathione is present after at least 8-12 hours following storage at 4° C. to 25° C. (Looker et al., 2008); (WO 2008/153762).

Although S-nitrosothiols, for example S-nitrosoglutathione, are attractive for treating a variety of diseases, solid oral dose formulations are unsuitable, as they decompose rapidly under physiological conditions and are not able to deliver sufficient quantities of the active moiety, NO, to the desired location for extended periods of time or in a controlled manner. Parenteral injectable solutions offer a suitable form of administration and continuous infusion allows sufficient quantities of S-nitrosothiols to reach the desired location rapidly for extended periods of time and in a controlled manner. The extreme labile nature of S-nitrosothiols, such as S-nitrosoglutathione, in solution prevents formulation directly as a "ready to use liquid dosage form". As such, the solution would need to be made up immediately (extemporaneously) from the S-nitrosothiol solid dry particles, prior to administration.

Parenteral dosage forms differ from all other dosage forms in that they must be sterile (absent of viable microorganisms) and free from physical, chemical, and biological contaminants as they are administered by injection, infusion or implantation directly into the human or animal body. The pharmaceutical grade requirements for sterilisation of S-nitrosothiol parenteral products pose significant commercial development problems.

So-called final-filter devices for intravenous (IV) administration include filters attached to the end of the tubing of an IV administration set for removing particulates and some microorganisms such as bacteria or fungi by filtration immediately prior to entry into the IV needle for administration. The use of filters having porosities in the sub–0.5-µm region (e.g. 0.22 µm) enables, in principle, bacteria and fungi to be removed. However, the use of final-filter devices carries associated problems. Firstly, some bacteria and fungi, that are not uniformly sized or spherical, could pass through the filter membrane, as could viruses and mycoplasmas. In addition, when low concentrations of a drug are present in the solution for injection, absorption of the drug onto the filter membrane can lead to inadvertent underdosing of drug. Furthermore, fine filters when wet cannot pass air except under elevated pressure, which can lead to retention of air bubbles in the tubing during set-up and a consequent risk of injection of air to the patient during use when injection pressure is applied. The use of final-filter devices increases equipment costs, it creates a need for a constant supply of specialised consumables, and it creates a requirement for special training of regular healthcare personnel or the employment of specialists. Finally, regulatory authorities require stringent controls of this procedure and do not consider it as providing a sterile parenteral solution but only a step that would remove particulate matter.

The European Medicines Agency (EMA) has published guidelines for the selection of the most appropriate sterilisation method for a range of medicinal products. For dry powders, the preferred method according to the guidelines is sterilisation by dry heat in the sealed final container (terminal sterilisation); however, for thermosensitive medicinal products such as S-nitrosothiols, this sterilisation method would not be feasible, as the S-nitrosothiol would decompose. An alternative approach would be radiosterilisation (sterilisation by exposure to ionising electromagnetic radiation) (CPMP/QWP/054/98 corr). Sterilisation by irradiation also provides legal proprietary benefits to drug developers—the US Food and Drug Administration (FDA) categorises drugs which have been sterilised by irradiation as new drugs, meaning that an approved new drug application is required for marketing (21 CFR 310.502(a)(11)). However, S-nitrosothiols are also extremely sensitive to electromagnetic radiation, being also highly labile following free radical exposure. Indeed, an attempt to sterilise an injectable formulation of S-nitrosoglutathione within septum-sealed vials using gamma radiation was apparently unsuccessful as it was reported that an unexpected inorganic nitrate impurity was generated (Lin, et al, 2005). Furthermore, sulphur amino acids (such as cysteine in S-nitrosoglutathione) have been reported to be particularly sensitive to irradiation leading to degradation at gamma radiation levels as low as 5 kGy, possibly due to susceptibility to free radical attack (Ahn et al., 2002).

The sensitivity of S-nitrosothiols towards temperature and ionising electromagnetic radiation has hitherto prevented these methods being considered as realistic or reliable for preparing sterile, pharmaceutical grade, S-nitrosothiols. Like all methods of sterilisation, irradiation involves a compromise between inactivation of the contaminating microorganisms and damage to the product being sterilised. The imparted energy, in the form of gamma photons or electrons, does not particularly differentiate between molecules of the contaminating microorganism and those of the pharmaceutical product.

For these reasons and others, effective simple sterilisation of S-nitrosothiols such as, for example, S-nitrosoglutathione, in clinical grades of purity has been an insurmountable barrier, which has hindered the development of pharmaceutical uses of these potentially valuable drugs in human and veterinary medicine.

The present invention is based on our surprising finding that ionising radiation is effective to sterilise S-nitrosothiols with either no reduction in purity or a reduction in purity by not more than about 5.0% through degradation, so that these active agents, for example in the form of solid particles in a pre-metered dosage weight, preferably in medical vials or similar containers, can be sterilised in clinical grades of purity.

SUMMARY OF THE INVENTION

The present invention is as defined in the appended claims.

The present invention provides in a first aspect a sterile S-nitrosothiol or a sterile pharmaceutical pre-composition comprising S-nitrosothiol, wherein the S-nitrosothiol is in dry solid form.

The S-nitrosothiol or sterile pharmaceutical pre-composition comprising S-nitrosothiol is preferably contained prior to use in a dry sterile environment such as, for example, in a sealed container. The seal may be a simple seal whereby the container can be opened, for example pierced, under sterile conditions to allow the sterile S-nitrosothiol or a sterile pharmaceutical pre-composition comprising S-nitrosothiol to be formulated with one or more sterile pharmaceutical diluents, excipients, carriers, additional active agents, or any combination thereof, to make a final pharmaceutical composition for administration. The seal may be arranged, for example, so that a sterile liquid can be introduced into the container, for example using a syringe provided with a hollow needle, to dissolve or suspend the sterile dry solid S-nitrosothiol or the sterile pharmaceutical pre-composition in situ within the container. A conventional septum seal is an example of such a seal. In that case, the seal may further permit the sterile pharmaceutical solution or suspension thus formed to be withdrawn from the container for administration to the patient, for example using a syringe provided with a hypodermic needle. For storage and transportation, the sealed container containing the sterile dry solid S-nitrosothiol or the sterile pharmaceutical pre-composition can be provided with an impermeable sealing cap. Where a septum seal or the like is present which allows sterile liquid to be introduced and withdrawn from the sealed container without loss of sterility of the contents of the container, an impermeable sealing cap may suitably be provided for transportation and storage, to overlie the septum barrier or the like in conventional manner.

From this it will be seen that the expression "pharmaceutical pre-composition" as used herein refers particularly to a precursor to a pharmaceutical composition. The pharmaceutical pre-composition may itself comprise, in addition to the one or more S-nitrosothiol, one or more pharmaceutical diluents, excipients, carriers, additional active agents, or any combination thereof. The pharmaceutical pre-composition may itself be usable as a pharmaceutical composition if a dry solid composition is sufficient for the intended administration route, but more usually it is expected that the pharmaceutical pre-composition would be used to make up a final pharmaceutical composition ready-to-use, by mixture with one or more sterile pharmaceutical diluents, excipient, carriers, additional active agents, or any combination thereof, as will be described in more detail below.

The sterile dry solid S-nitrosothiol or sterile pharmaceutical pre-composition comprising sterile dry solid S-nitrosothiol, according to the first aspect of the present invention, is preferably obtained by exposing the dry solid S-nitrosothiol, or the pharmaceutical pre-composition comprising the dry solid S-nitrosothiol, in non-sterile form to a sterilising dose of ionising radiation in an environment sealed from external contamination. Such a method is new and constitutes a second aspect of the present invention. The exposure to the ionising radiation preferably takes place when the S-nitrosothiol or the pharmaceutical pre-composition comprising S-nitrosothiol in non-sterile form is in the same dry environment as it will be stored and transported prior to use, such as, for example, the sealed container described in relation to the first aspect of the present invention.

The sealed container and the environment within it may suitably be arranged to minimise degradation of the S-nitrosothiol during storage or transportation prior to use. For example, the walls of the sealed container may be tinted (e.g. amber-tinted) or opaque to light, to reduce or eliminate photodegradation of the S-nitrosothiol. The dry sterile environment within the sealed container may contain or consist of one or more of dry air, another dry gas such as, for example, a dry inert gas such as nitrogen, helium, argon, neon, xenon, krypton or a mixture thereof, and it may optionally be under a reduced pressure in comparison with the external ambient air, to reduce or eliminate contact between the S-nitrosothiol and moisture and/or oxygen. The sealed container may suitably contain a suitable desiccant in known manner to maintain dry conditions, for example by absorbing any residual moisture such as water of crystallisation or atmospheric moisture introduced by one or more of the contents of the container. Suitable desiccants that can be used in the present invention are those that are pharmaceutically safe, and include, for example, pharmaceutical grades of silica gel, crystalline sodium, potassium or calcium aluminosilicate, colloidal silica, anhydrous calcium sulphate and the like. The desiccant may be present in an amount from about 1.0% w/w to 20.0% w/w, or from about 2% w/w to 15% w/w, relative to the weight of S-nitrosothiol.

The sealed container may contain one or more oxygen scavengers in known manner.

The S-nitrosothiol containing material, both before and after sterilisation, is suitably stored in the dark and exposed to light as little as possible. Tinted or light-opaque containers such as amber-tinted glass vials are conveniently used to contain the material in dry form. Overwraps or pouches that are impermeable to oxygen and light, for example aluminum pouches, may be used in known manner to further protect the S-nitrosothiol against degradation.

The dry solid S-nitrosothiol or the pharmaceutical pre-composition comprising dry solid S-nitrosothiol may suitably be present in the container in a metered dose, for example, a known weight of S-nitrosothiol selected according to an ultimate medical use. Instructions for mixing with a one or more sterile pharmaceutical diluents, excipients, carriers, additional active agents, or any combination thereof—for example, a sterile liquid or paste or gel, such as sterile saline, or other solid excipients or carriers—to obtain the pharmaceutical composition in a desired concentration for use may suitably be provided. In a third aspect the present invention provides a kit comprising a container or containers containing sterile S-nitrosothiol or a sterile pharmaceutical pre-composition comprising S-nitrosothiol according to the first aspect of the invention together with instructions for mixing the sterile S-nitrosothiol or a sterile pharmaceutical pre-composition comprising S-nitrosothiol with one or more sterile pharmaceutical diluents, excipients, carriers, additional active agents, or any combination thereof, to obtain a pharmaceutical composition for a pharmaceutical use containing S-nitrosothiol in a desired concentration.

When the sterile dry solid S-nitrosothiol or the sterile pharmaceutical pre-composition comprising the sterile dry solid S-nitrosothiol is prepared by exposing dry solid S-nitrosothiol, or the pharmaceutical pre-composition comprising dry solid S-nitrosothiol, in non-sterile form to a sterilising dose of ionising radiation in an environment sealed from external contamination, the resulting sterile material may contain dead microbial cells killed by the ionising radiation and the nature and concentration of any impurities will be characteristic of radiosterilised S-nitrosothiol wherein the sterilisation is performed on dry solid material in accordance with the invention. The products prepared or preparable by this process, as well as final pharmaceutical compositions made up from the sterile materials, can be identified in this way.

The sterile dry solid S-nitrosothiol or the sterile pharmaceutical pre-composition comprising sterile dry solid S-nitrosothiol may suitably have an S-nitrosothiol purity of at least about 95.0%, for example at least about 98.0%, for example at least about 98.5%, for example at least about 99.0%, for example at least about 99.5%. In the case of the sterile pharmaceutical pre-composition, "S-nitrosothiol purity" refers to the purity of the solid S-nitrosothiol material disregarding any other components of the pharmaceutical pre-composition.

The dry solid S-nitrosothiol, whether alone or as part of a pharmaceutical pre-composition, is preferably in particulate form, that is, as a population of particles of S-nitrosothiol. The particles of S-nitrosothiol may suitably comprise crystals.

The method of the second aspect of the present invention, comprising exposing dry solid S-nitrosothiol, or a pharmaceutical pre-composition comprising dry solid S-nitrosothiol, in non-sterile form to a sterilising dose of ionising radiation in an environment sealed from external contamination, may be performed under conditions such that there is no reduction of the purity of the S-nitrosothiol or that its purity is reduced by not more than about 5.0% through degradation. Thus, for example, starting from materials in which the S-nitrosothiol has a purity of about 99.5% purity, the conditions of the process should be such that the reduction of S-nitrosothiol purity is not more than about 1.5%, so that the sterile product has an S-nitrosothiol purity of at least about 98.0%.

We have found that the purity of S-nitrosothiol in the solid dry material can be maintained to at least about 95.0%, and/or that any drop in purity of the S-nitrosothiol in the solid dry material can be maintained to not more than about 5.0%, for example not more than about 2.0%, for example not more than about 1.5%, when the temperature of the S-nitrosothiol is maintained not greater than about 40° C. during the sterilising exposure to the ionising radiation.

A suitable sterilising dose of the ionising radiation is an absorbed dose of up to about 50 kGy, up to about 35 kGy, up to about 25 kGy, up to about 15 kGy, or up to about 5 kGy to sterilise the S-nitrosothiol. In the method the S-nitrosothiol may, for example, be exposed to the sterilising dose of ionising radiation for a time period less than about 24 hours; for example less than about 18 hours; for example less than about 12 hours; for example less than about 10 hours; for example less than about 6 hours; for example less than about 3 hours; for example less than about 2 hours; for example less than about 1 hour; for example less than about 45 minutes; for example less than about 30 minutes; for example less than about 15 minutes; for example less than about 2 minutes; for example less than about 1 minute; for example less than about 45 seconds; for example less than about 30 seconds.

In a fourth aspect the present invention provides a method for preparing a sterile pharmaceutical composition for human or veterinary use, comprising mixing the said sterile S-nitrosothiol or the sterile pre-composition containing S-nitrosothiol with one or more sterile pharmaceutical diluents, excipients, carriers, additional active agents, or any combination thereof—for example, a sterile liquid, paste or gel or other solid excipients or carriers and optionally one or more other ingredients—to provide a sterile S-nitrosothiol-containing pharmaceutical composition for therapeutic or prophylactic use. The present invention also provides in a further aspect an S-nitrosothiol-containing pharmaceutical composition so formed or formable.

The final S-nitrosothiol-containing pharmaceutical composition for therapeutic or prophylactic use may be for use in a method of human or veterinary therapy or prophylaxis. The method of therapy or prophylaxis may, for example, involve inducing arterial or venous smooth muscle relaxation, reducing augmentation index, reducing augmentation pressure, reducing arterial stiffness, inhibiting platelet aggregation, inducing T cell apoptosis and activating guanylate cyclase in a human or animal, or may be a method of treating or preventing a disease or disorder which responds to S-nitrosothiol or NO therapy, for example pre-eclampsia, severe pre-eclampsia, eclampsia, HELLP syndrome, organ transplantation perfusion, organ dialysis, post-operative conditions of balloon angioplasty, acute myocardial infarction, unstable angina, cerebral embolism, hypertension, atherosclerosis, restenosis, ischemia and heart failure, other cardiovascular proliferative, inflammatory, contractile and hypertensive disorders, and pre-conditioning related disorders of the heart and brain, esophageal spasm, biliary spasm, colic and other motility and smooth muscle disorders of the gastrointestinal tract, erectile dysfunction, stroke, bronchial constriction, cystic fibrosis, pneumonia, asthma, pulmonary fibrosis, and other pulmonary disorders involving diminished gas exchange or inflammation, as well as infectious diseases of viral, bacterial and other origin, disorders of red blood cells characterised by S-nitrosothiol deficiency, abnormal rheology or impaired vasodilation (such as sickle cell disease and stored blood-related diathesis), and thrombotic disorders.

The ionising radiation may be selected from electron beam radiation, gamma radiation and X-rays.

Electron beam (e-beam) radiation is characterised by low penetration and high dosage rates and requires the shortest exposure times in order to irradiate the S-nitrosothiol; the time of exposure to the sterilising dose of ionising radiation in the case of e-beam radiation may, for example, be less than about 1 hour; for example less than about 45 minutes; for example less than about 30 minutes; for example less than about 15 minutes; for example less than about 2 minutes; for example less than about 1 minute; for example less than about 45 seconds; for example less than about 30 seconds.

Gamma radiation is characterised by high penetration and low dosage rates and provides homogenous irradiation that requires longer exposure time; the time of exposure to the sterilising dose of ionising radiation in the case of gamma radiation may, for example, be less than about 24 hours; for example less than about 18 hours; for example less than about 12 hours; for example less than about 10 hours; for example less than about 6 hours; for example less than about 3 hours; for example less than about 2 hours; for example about 1 hour; and typically at least about 1 hour.

The temperature of the S-nitrosothiol or S-nitrosothiol-containing material during the exposure to the ionising radiation is preferably in the range of about −100° C. to about +40° C. A temperature in the range of about −80° C. to about +35° C. is particularly suitable. The temperature may be allowed to fluctuate during the irradiation, subject to not exceeding about (+)40° C., which can be ensured by performing the irradiation in a temperature-controlled container. However, we have found that very good results are achieved by positive cooling of the S-nitrosothiol to restrict elevation of temperature during irradiation, for example to a temperature in the range of about −80° C. to about +35° C., for example from about −80° C. to about +30° C., for example not greater than about 30° C., for example not greater than about 28° C., for example not greater than about 20° C., for example not greater than about 15° C., for example not greater than about 10° C., for example not greater than about 0° C., for example not greater than about −30° C., for example not greater than about −60° C., for example not greater than about −70° C., during the sterilising exposure to the ionising radiation.

The method of preparing the sterile dry solid S-nitrosothiol or a sterile dry solid pharmaceutical pre-composition comprising S-nitrosothiol according to the second aspect of the present invention may suitably be performed using electron beam radiation at an absorbed dose of up to about 50 kGy, for example at about 5 kGy (e.g. about 3 to about 7 kGy), or at about 15 kGy (e.g. about 13 to about 17 kGy), or at about 25 kGy (e.g. about 23 to about 27 kGy), or at about 35 kGy (e.g. about 33 to about 37 kGy), or at about 50 kGy (e.g. about 47 to about 53 kGy), the temperature of the material to be sterilised starting at room temperature conditions (about 18 to about 24° C.) but with freedom to fluctuate higher, and the exposure to the e-beam radiation taking place over up to about be less than about 1 hour; for example up to about 45 minutes; for example up to about 30 minutes; for example up to about 15 minutes; for example up to about 2 minutes; for example up to about 1 minute; for example up to about 45 seconds; for example up to about 30 seconds. The maximum temperature of the material to be sterilised may suitably be controlled to not greater than about 40° C., for example not greater than about 35° C., for example not greater than about 30° C., for example not greater than about 28° C., for example not greater than about 20° C.

In another embodiment, the method of preparing the sterile dry solid S-nitrosothiol or a sterile dry solid pharmaceutical pre-composition comprising S-nitrosothiol according to the second aspect of the present invention may suitably be performed using electron beam radiation at an absorbed dose of up to about 50 kGy, for example at about 5 kGy (e.g. about 3 to about 7 kGy), or at about 15 kGy (e.g. about 13 to about 17 kGy), or at about 25 kGy (e.g. about 23 to about 27 kGy), or at about 35 kGy (e.g. about 33 to about 37 kGy), or at about 50 kGy (e.g. about 47 to about 53 kGy), the temperature of the material to be sterilised being maintained at a temperature below about 35° C., for example below about 30° C., for example below about 28° C., for example below about 20° C., for example below about 15° C., for example below about 5° C., for example below about 0° C., for example below about −30° C., for example below about −60° C., for example below about −70° C., for example at about −80° C., and the exposure to the radiation taking place over up to about 1 hour, for example up to about 45 minutes, for example up to about 30 minutes, for example up to about 15 minutes, for example up to about 2 minutes, for example up to about 1 minute, for example up to about 45 seconds, for example up to about 30 seconds.

In another embodiment, the method of preparing the sterile dry solid S-nitrosothiol or a sterile dry solid pharmaceutical pre-composition comprising S-nitrosothiol according to the second aspect of the present invention may suitably be performed using gamma radiation at an absorbed dose of up to about 50 kGy, for example at about 5 kGy (e.g. about 3 to about 7 kGy), or at about 15 kGy (e.g. about 13 to about 17 kGy), or at about 25 kGy (e.g. about 23 to about 27 kGy), or at about 35 kGy (e.g. about 33 to about 37 kGy), or at about 50 kGy (e.g. about 47 to about 53 kGy), the temperature of the material to be sterilised being maintained at a temperature below about 35° C., for example below about 30° C., for example below about 30° C., for example below about 28° C., for example below about 20° C., for example below about 15° C., for example below about 5° C., for example below about 0° C., for example below about −30° C., for example below about −60° C., for example below about −70° C., for example at about −80° C., and the exposure to the radiation taking place over up to about 24 hours; for example up to about 18 hours; for example up to about 12 hours; for example up to about 10 hours; for example up to about 6 hours; for example up to about 3 hours; for example up to about 2 hours; for example about 1 hour; and typically at least about 1 hour.

We have found that sterilisation using gamma radiation, with the material to be sterilised starting at room temperature conditions (about 18 to about 24° C.) but with freedom to fluctuate higher, could require an exposure to the radiation for more than about 1 hour, for example from about 1 to about 24 hours; for example up to about 18 hours; for example up to about 12 hours; for example up to about 10 hours; for example up to about 6 hours; for example up to about 3 hours; for example up to about 2 hours. In addition, such long exposure to gamma radiation without temperature control has the undesirable consequence that the temperature can rise above about 40° C., for example to about 60° C., and the purity of the S-nitrosothiol can consequently be reduced, for example by about 4 to about 10% relative to a non-irradiated matching control.

Surprisingly, the method of second aspect of the present invention sterilises the S-nitrosothiol, for example S-nitrosoglutathione, without reduction of the purity by more than about 5.0% through degradation. Because the degradation of S-nitrosothiols proceeds via homolytic fission of the S—NO bond to release NO at high quantum yields (0.2 to 0.8), and is induced by relatively low energy electromagnetic radiation such as UV light or sunlight (Manoj et al., 2009) it would have been expected that degradation would have been significant under exposure to ionising radiation. Maintenance of a low temperature (positive cooling) alongside short irradiation time intervals and light protective storage containers has, however, been found to suppress the tendency for the molecules to degrade, preserving high purity for pharmaceutical use.

The expressions "sterile", "sterilise" and related expressions used herein refer to a level of sterility (absence of microorganisms) which satisfies the requirements of the European Medicines Agency (EMA) for sterility of pharmaceutical and veterinary products. The sterility assurance level (SAL) refers to the probability of a single unit (for example, the interior surface and all contents of a vial, ampoule, bag or other container containing solid S-nitrosothiol-containing material and a gas-filled space above) being non-sterile after it has been subjected to sterilisation. In the present invention, a unit "is sterile" or "has been sterilised" if the SAL is less $10^{-6}$ or lower, i.e. that one in a million of those units or fewer would be non-sterile.

DETAILED DESCRIPTION OF THE INVENTION

S-Nitrosothiols

S-nitrosothiols used in the present invention may, for example, be selected from the following or any combination of one or more thereof:
S-nitrosoglutathione (GSNO)
S-nitroso-L-cysteine (CySNO)
S-nitroso-N-acetyl-cysteine (SNAC)
S-nitroso-L-cysteinemethyl-ester (CMESNO)
S-nitroso-D,L-penicillamine (PSNO)
S-nitroso-N-acetyl-D,L-penicillamine (SNAP)
S-nitroso-N-acetylcysteamine (ACSNO)
S-nitroso-beta-mercaptosuccinic acid
1-S-nitrosothio-beta-D-galactopyranose
S-nitrosothioglycerol
S-nitrosohomocysteine
S-nitrosocysteinylglycine
S-nitrosocaptopril
alkyl, cycloalkyl or aryl thionitrites, such as, for example, methyl thionitrite, ethyl thionitrite, n-propyl thionitrite, s-propyl thionitrite, n-butyl thionitrite, s-butyl thionitrite, tert-butyl thionitrite, n-pentyl thionitrite, n-hexyl thionitrite, cyclohexyl thionitrite, phenyl thionitrite
S-nitroso derivatives of cysteine-containing proteins, oligo- and poly-peptides, for example S-nitrosoalbumin, poly-S-nitrosoalbumin or S-nitrosohemoglobin
and any derivative thereof
and a salt of any of the foregoing.

A preferred S-nitrosothiol used in the present invention is S-nitrosoglutathione (GSNO) or a derivative or salt thereof. A synthesis of S-nitrosoglutathione and S-nitroso-L-cysteine from respectively glutathione and L-cysteine is described by Hart (1985).

The expression "derivative" used herein to refer to S-nitrosothiols, particularly means a compound which retains the characteristic —S—N═O moiety but differs from the named S-nitrosothiol in one or more of the following respects, and preferably only in that or those respects:
a hydrocarbyl moiety is substituted by one or more of the following substituents: one or more halogen atom; one or more hydroxyl group; one or more $C_{1-8}$ alkyl group; one or more $C_{2-8}$ alkenyl group; one or more $C_{2-8}$ alkynyl group; one or more $C_{1-8}$ alkoxy group; one or more enol ether group —C═C(OR) wherein preferably R is selected from hydrogen, alkyl, alkenyl, alkynyl, aryl, heteroaryl, aralkyl, heteroalkyl, cycloalkyl and heterocyclyl; one or more enol ester group —C═C(OC(O)R) wherein preferably R is selected from hydrogen, alkyl, alkenyl, alkynyl, aryl, heteroryl, aralkyl, heteroalkyl, cycloalkyl and heterocyclyl; one or more carboxylate group; one or more esterified carboxylate group;
a hydroxyl moiety is esterified;
a compound is prepared as a hydrate, solvate or metal chelate, or any prodrug form.

In the foregoing paragraph, the expression "esterified" includes without limitation the esters selected from alkyl, alkenyl, alkynyl, aryl, heteroaryl, aralkyl, heteroalkyl, cycloalkyl and heterocyclyl esters of acidic groups such as, for example, carboxylic acids, phosphoric acids, phosphinic acids, sulfonic acids, sulfinic acids and boronic acids.

Salt forms of S-nitrosothiols include compounds which differ from the named S-nitrosothiol in that any acid group or moiety of the S-nitrosothiol is present in the form of a salt formed with a suitable base and/or any basic group or moiety of the S-nitrosothiol is present in the form of a salt formed with a suitable acid. Bases that may be used to form salts with S-nitrosothiols containing suitable acid groups include, for example, bases such as sodium hydroxide, potassium hydroxide, lithium hydroxide, barium hydroxide, calcium hydroxide, magnesium hydroxide, transition metal hydroxides such as zinc hydroxide, ammonia, organic amine bases (such as, for example, N,N'-dibenzylethylenediamine, chloroprocaine, choline, hydroxyalkylamines such as diethanolamine, ethylenediamine, N-methylglucamine, procaine, N-benzylphenethylamine, 1-p-chlorobenyl-2-pyrrolidin-1'-yl-methylbenzimidazole, alkylamines such as diethylamine, piperazine and tris(hydroxymethyl)aminomethane), sodium carbonate and sodium bicarbonate. Acids that may be used to form salts with S-nitrosothiols containing suitable basic groups include, for example, acids such as hydrochloric acid, hydrobromic acid, sulphuric acid, nitric acid, phosphoric acid, acetic acid, citric acid, lactic acid, maleic acid, ascorbic acid, succinic acid, butyric acid, valeric acid, fumaric acid, tartaric acid and propionic acid.

The above compounds are known or may readily be prepared from available sources by standard chemical synthetic methods well known in the art. For pharmaceutical use the compounds may be administered to animals and humans in suitable dosages without toxic effects and are either pharmaceutically active or are prodrugs of pharmaceutically active compounds.

Purity Levels and Measurement, Impurities

The S-nitrosothiol used in the present invention may contain a limited amount of impurities. It is preferred that the S-nitrosothiol, for example S-nitrosoglutathione, has a purity greater than or equal to about 95.0% as determined by known methods in the art, for example high performance liquid chromatography (HPLC) or direct UV adsorption (A 210-335 nm).

In one embodiment, the S-nitrosothiol used in the present invention, for example S-nitrosoglutathione, has a purity ranging from about 95.0% to about 100.0% or any value within that range, for example at least about 97.0%, or at least about 98.0%, or at least about 99.0%.

The sterilisation method according to the present invention preferably sterilises the S-nitrosothiol without reduction of the purity by more than about 5.0% through degradation. Degradation, if it occurs, is detectable by an increase in the products of one or more of unimolecular homolytic scission of the S-nitrosothiol at the S—N bond, enzymatic degradation, reductive degradation and oxidative degradation (decomposition). Such detection of degradation products may be performed by known methods in the art, for example high performance liquid chromatography (HPLC) or direct UV adsorption (A 210-335 nm).

Impurities present in the S-nitrosothiol can typically include the corresponding denitrosated compound with or without oxidation or reduction. The principal impurities arising in any particular S-nitrosothiol can be readily ascertained by chemical analysis. For example common impurities of S-nitrosoglutathione include glutathione (GSH) and glutathione disulfide (GSSG). In an embodiment, the compounds and formulations used in the present invention contain total impurities (including reduced and oxidised L-glutathione) in a range of from about 0.0% to about 5.0% or any specific value within that range, for example less than about 3.0% or less than about 2.5% or less than about 2.0%.

Sterility Levels and Measurement

The dose of radiation to sterilise the S-nitrosothiol can be determined by methods well known in the art. ISO 11137-2:2013 specifies methods for determining the minimum dose needed to achieve a specified requirement for sterility and methods to substantiate the use of 25 kGy or 15 kGy as the sterilisation dose to achieve a sterility assurance level, SAL, of $10^{-6}$. ISO 11137-2:2013 also specifies methods of sterilisation dose audit used to demonstrate the continued effectiveness of the sterilisation dose. The EMA, the European Pharmacopoeia and the US Pharmacopeia typically expect a radiation dose of ≥25 kGy as the reference sterilisation dose to achieve a sterility assurance level (SAL) of $10^{-6}$.

A suitable radiation dose for the present invention is 15-35 kGy. However, this sterilisation dose can be varied according to the ISO 11137-2:2013 guideline (for example, 5-50 kGy could be used if suitably justified).

The radiation dose used in the present invention should be such as to achieve a Sterility Assurance Level (SAL) of $10^{-6}$, namely a probability of one in a million that a single sterilised vial of pharmaceutical material is non-sterile after treatment.

Ionising Radiation and Sources

Sterilisation by irradiation involves a compromise between inactivation of the contaminating microorganisms and damage to the product being sterilised.

Gamma radiation is characterised by its deep penetration and low dosage rates. The energy of gamma radiation, as electromagnetic quantum waves, is similar to light, but with higher photon energy and shorter wavelength. The interaction between high-energy gamma radiation and matter forms ion pairs by ejecting electrons, leading to free-radical formation and excitation. The free radicals are extremely reactive because each has an unpaired electron on one of its outer orbitals. Free-radical reactions may involve gas liberation, double-bond formation and scission, exchange reactions, electron migration, and cross-linking. In fact, any chemical bond may be broken and any potential chemical reaction may take place. In crystalline materials, this may result in vacancies, interstitial atoms, collisions, thermal spurs, and ionising effects.

Gamma irradiators are powered by Cobalt-60, effectively killing microorganisms throughout the product and its packaging. The amount of radiation received depends on the type of product and its dose requirements.

E-Beam radiation is a form of ionising energy that is characterised by its low penetration and high dosage rates. The "beam" (a concentrated, highly charged stream of electrons) is generated by accelerators capable of producing continuous or pulsed beams. As the product being sterilised passes beneath or in front of the e-beam, energy from the electrons is absorbed, altering various chemical and biological bonds and destroying the DNA and reproductive capabilities of microorganisms.

X-ray radiation is a further form of ionising electromagnetic radiation. Whereas gamma radiation originates in the nucleus, X-rays originate in the electron fields surrounding the nucleus or are machine-produced.

Apparatus and facilities for providing ionising radiation for sterilisation of chemicals, for example gamma radiation, e-beam radiation or X-ray radiation, are well known and commercially available.

The radiation dosage applied in the method according to the present invention is preferably monitored using a dosimeter. Dosimeters are commercially available and will be known to those skilled in the art. Dosimetrically monitored application of radiation allows products to be processed, verified and immediately released for shipment.

In the method of the present invention it is preferred that the ionising radiation is applied so as to give a reproducible sterilisation dose. Gamma radiation is well suited to irradiating a large batch over a few hours cycle. E-beam is a continuous process that can deliver a required dose in a few seconds as individual boxes pass by the e-beam accelerator.

We have found particularly in the present invention that certain controlled conditions for gamma and e-beam irradiations result in a surprisingly low degree of product degradation, enabling the purity of the initial chemical to be effectively maintained through to the sterile product for medical or other physiological use.

Apparatus and Method for Performing the Invention

The sterilising method of the present invention is suitably performed in an apparatus comprising:
- a support system for supporting the material to be sterilised in an appropriate container;
- an ionising radiation source adapted to irradiate a radiation field;
- a drive system adapted to cause relative movement of the container holding the material within the radiation field, to permit even distribution of the radiation;
- a dosimeter system to measure the radiation dose absorbed by the material in the container;
- a temperature control system to provide a desired temperature around the container holding the material; and
- means to terminate the application of the radiation to the container when the required sterilising dosage is achieved.

Apparatus of this general type are commercially available and do not require detailed description.

Temperature Control

It is well known to those skilled in the art that irradiation can elevate the temperature of the irradiated material. The temperature of the S-nitrosothiol-containing material during the exposure to the ionising radiation is preferably maintained in the range of about $-100°$ C. to not greater than $+40°$ C. A temperature in the range of about $-80°$ C. to about $+35°$ C. is particularly suitable. The temperature may be allowed to fluctuate during the irradiation, preferably subject to not exceeding about $(+)40°$ C., which can be ensured by performing the irradiation in a temperature-controlled container. However, we have found that very good results are achieved by maintaining the temperature during irradiation within a defined range by positive temperature control or cooling of the S-nitrosothiol-containing material, for example to a temperature in the range of about $-80°$ C. to about $+35°$ C., for example not greater than about $30°$ C., not greater than about $28°$ C., not greater than about $20°$ C., not greater than about $15°$ C., not greater than about $10°$ C., not greater than about $5°$ C., not greater than about $0°$ C., for example not greater than about $-30°$ C., for example not greater than about $-60°$ C., for example not greater than about $-70°$ C., during the sterilising exposure to the ionising radiation.

For commercial use, for example on a large batch scale or in a continuous production process, conventional thermostatically controlled containers with appropriate refrigeration or cryoengineering systems may be used in the performance of the present invention, to achieve and maintain the desired temperature conditions for the irradiation.

On a small batch scale, dry ice (solid $CO_2$) at $-80°$ C., water ice at $0°$ C., or other cold materials at known temperatures, are effective to establish and maintain a desired temperature in the range of about $+40°$ C. to about $-80°$ C. for irradiation, as will be illustrated by way of non-limiting example in Example 2 below.

Pharmaceutical Compositions and Formulations

The sterile dry solid S-nitrosothiol or the sterile pharmaceutical pre-composition used in the present invention is preferably formulated so that, on mixing with a suitable sterile diluent, excipient and/or carrier, for example a liquid, paste or gel or other solid excipients or carriers, to dissolve or disperse the dry solid material without loss of sterility, and optionally mixing with one or more additional ingredients, a sterile pharmaceutical formulation is thus formed which is compatible with the intended treatment or prophylaxis and the intended route of administration. Examples of routes of administration include parenteral (for example, intravenous), intradermal, subcutaneous, inhalation, transdermal (topical), transmucosal (gingival or buccal), vaginal and rectal administration routes.

The total of (a) the dry solid material according to the first aspect of the present invention and (b) the sterile liquid and any optional additional ingredient(s), a sterile S-nitrosothiol-containing pharmaceutical composition is prepared from the sterilised S-nitrosothiol or pre-pharmaceutical composition according to the first aspect of the present invention. It is preferred that the sterile S-nitrosothiol-containing pharmaceutical composition will be prepared in this way shortly before administration to a human or animal patient.

The required ingredients for the total final composition, as well as their distribution between the dry solid material according to the first aspect of the present invention, the sterile liquid to be mixed therewith and any optional additional ingredient(s) to be mixed with either or both of the foregoing during the method of making-up the final pharmaceutical composition, will be well known to those skilled in the art or readily decided on a case by case basis by those skilled in the art following normal formulation practice. For example, as is well known, final ready-to-use solutions or suspensions can include one or more of the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose.

A sterile pre-composition of the present invention, or a non-sterile pre-composition prepared to be sterilised in accordance with the present invention, or a sterile composition after being made up for administration using a sterile S-nitrosothiol or sterile pre-composition according to the present invention, will thus comprise at least one S-nitrosothiol in combination with at least one pharmaceutically acceptable diluent, excipient, carrier, additional active agent, or any combination thereof. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable diluents, excipients and carriers are described in Remington: The Science and Practice of Pharmacy, $22^{nd}$ Edition, 2012, Pharmaceutical Press, which is incorporated herein by reference. Examples of such diluents, excipients and carriers include, but are not limited to, water, saline, Ringer's solutions, dextrose solution, and 5% human serum albumin. Liposomes and non-aqueous vehicles such as fixed oils may also be used. Pharmaceutically acceptable carriers can also include solid carriers such as lactose, terra alba, sucrose, talc, gelatin, agar, pectin, acacia, magnesium stearate, stearic acid and the like. Exemplary liquid carriers include syrup, peanut oil, olive oil, water and the like.

An excipient or carrier may include time-delay material known in the art, such as glyceryl monostearate or glyceryl distearate, alone or with a wax, ethylcellulose, hydroxypropylmethylcellulose, methylmethacrylate or the like. Other fillers, diluents, flavorants, and other additives such as are known in the art may also be included in a sterile pre-composition of the present invention, or a non-sterile pre-composition prepared to be sterilised in accordance with the present invention, or a sterile composition after being made up for administration using a sterile S-nitrosothiol or sterile pre-composition according to the present invention. The use of such media and agents for pharmaceutically active substances is well known in the art. Except insofar as any conventional media or agent is incompatible with the active compound, use thereof in the compositions is contemplated. More than one S-nitrosothiol can be present in the compositions and pre-compositions, according to clinical need of the patient. One or more supplementary physiologically active compounds, of a class other than the S-nitrosothiols, can also be incorporated into the compositions and pre-compositions.

The made up pharmaceutical compositions suitable for parenteral use typically include suitable carriers selected from physiological saline, bacteriostatic water, Cremophor EL (BASF, Parsippany, N.J.) and phosphate buffered saline (PBS). In all cases, the composition as administered must be sterile and should be fluid to the extent that easy syringability exists. A carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

For administration by inhalation, the made up compositions can be capable of being delivered in the form of a fine particulate powder or an aerosol spray from pressured container or dispenser that contains a suitable propellant, e.g., a gas such as carbon dioxide, or a nebulizer.

For transmucosal or transdermal administration, penetrants appropriate to the barrier to be permeated are suitably included in the made up compositions. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the S-nitrosothiol(s) and any other active ingredient(s) are suitably formulated into ointments, salves, gels, or creams as generally known in the art.

The final compositions can be prepared in the form of suppositories (e.g., with conventional suppository bases such as cocoa butter and other glycerides) or retention enemas for rectal delivery.

The final compositions may comprise a stabilizing buffer and can further comprise a surfactant. The buffer and/or surfactant or ingredients thereof may if desired be present in the sterile pre-composition of the present invention or a non-sterile pre-composition prepared to be sterilised in accordance with the present invention, or may be added when making up the sterile final composition for administration from a sterile S-nitrosothiol or sterile pre-composition according to the present invention. The amount of surfactant that can be present can range from about 0.1% w/w to about 10% w/w with respect to the S-nitrosothiol. In an embodiment, the amount of surfactant present is at least 1% w/w with respect to the S-nitrosothiol. In an embodiment, the amount of surfactant present is up to about 5% w/w with respect to the S-nitrosothiol. Examples of suitable surfactants include, but are not limited to, fatty acid, fatty acid esters including fatty acid triglycerides, fatty alcohols, salts of fatty acids, oleyl alcohol, sorbitan mono-oleate, sorbitan monolaurate, polyoxyethylene (20) sorbitan monolaurate, polyoxyethylene (20) sorbitan mono-oleate, natural lecithin, oleyl polyoxyethylene (2) ether, stearyl polyoxyethylene (2) ether, lauryl polyoxyethylene (4) ether, block copolymers of oxyethylene and oxypropylene, oleic acid, salts of oleic acid, synthetic lecithin, diethylene glycol dioleate, tetrahydrofurfuryl oleate, ethyl oleate, isopropyl myristate, isopropyl palmitate, glyceryl mono-oleate, glyceryl monostearate, glyceryl monoricinoleate, cetyl alcohol, stearyl alcohol, cetyl pyridinium chloride, olive oil, glyceryl monolaurate, corn oil, cotton seed oil, sunflower seed oil, polyoxyethylenesorbitan monooleate, sorbitan trioleate, oligolactic acid, lecithin, (poly)alkoxy derivatives including polyalkoxy alcohols, in particular 2-(2-ethoxyethoxy) ethanol. Additional (poly)alkoxy derivatives include polyoxyalkyl ethers and esters, such as polyoxyethylene ethers and esters, including, but not limited to, polyoxyethylene alkyl ethers, polyoxyethylene sorbitan fatty acid esters and polyoxyethylene stearates.

The final compositions may optionally comprise additional ingredients in known manner, such as additives that serve as preservatives, antioxidants, radical quenchers, pharmaceutically active agents, adjuvants, carriers, chemical stabilizers, and/or polymers. Such optional additional ingredients or some of them may if desired be present in the sterile pre-composition of the present invention or a non-sterile pre-composition prepared to be sterilised in accordance with the present invention, or may be added when making up the sterile final composition for administration from a sterile S-nitrosothiol or sterile pre-composition according to the present invention. The amount of additional ingredients included in a final made up formulation of an S-nitrosothiol can be, for example, 0% to about 1% w/w.

It is especially advantageous to formulate final ready to use compositions in dosage unit form for ease of administration and uniformity of dosage. "Dosage unit form" as used herein refers to physically discrete units suited as unitary dosages for the subject to be treated, each unit containing a predetermined quantity of active agent calculated to produce the desired therapeutic effect, in association with the required one or more pharmaceutical carriers, excipients, diluents, additional active agents, or any combination thereof. As is well known to those skilled in the art, the specifications for dosage unit forms are dictated by and directly dependent on the unique characteristics of the active S-nitrosothiol agent and the particular therapeutic effect to be achieved, and the limitations inherent in the art of compounding such an active agent for the treatment of individuals.

The dry solid material of the present invention—that is, the sterile dry solid S-nitrosothiol, for example S-nitrosoglutathione, or the sterile dry solid pre-composition containing S-nitrosothiol, for example S-nitrosoglutathione—can be present in a measured weight so that, after making up into the final sterile pharmaceutical composition for administration, the final composition for administration contains a unit dose of the S-nitrosothiol active agent or a multiple of the said unit dose such that portions of the final composition can be administered sequentially before a new composition needs to be made up from dry solid material.

For this purpose, the measured weight of the dry solid material—that is, the sterile dry solid S-nitrosothiol, for example S-nitrosoglutathione, or the sterile dry solid pre-composition containing S-nitrosothiol, for example S-nitrosoglutathione—is enclosed in single dose or multiple dose containers such as single dose or multiple dose vials, single dose ampoules, single dose or multiple dose bags or disposable single dose syringes which containers can in each case, for example, in each case be made of glass or plastic or a combination thereof. As previously mentioned, because S-nitrosothiols (for example, S-nitrosoglutathione) are light sensitive, the components of the dose containers have suitable overwraps or are protected from light, for example being tinted or opaque. All handling equipment and containers for the pharmaceutical compositions, or any intermediate formulations in the route to prepare the pharmaceutical compositions such as sterile liquids, containing the S-nitrosothiol made up from the sterile dry solid material according to the present invention should similarly be tinted or opaque or provided with suitable overwraps to protect them from light. Such handling equipment and containers may, for example, include infusion lines and syringes.

Solid Forms

The dry solid S-nitrosothiol (for example, S-nitrosoglutathione) or the dry solid pre-composition containing S-nitrosothiol (for example S-nitrosoglutathione) may suitably be processed in conventional manner prior to sterilisation, to produce particles in a desired size range. For example, the dry solid material can be milled or micronised using suitable equipment for example an air jet mill, hammer mill, ball mill or microniser.

Alternatively, particles in the desired particle range may be obtained by, for example, lyophilisation, spray drying or controlled crystallization methods, for example, crystallization using supercritical fluids.

The dry solid S-nitrosothiol (for example, S-nitrosoglutathione) particles or the dry solid pre-composition containing S-nitrosothiol (for example S-nitrosoglutathione) particles may, for example, have a weight average particle diameter in the range of about 0.1 μm to about 50 μm, for example about 0.2 μm to about 20 μm, or about 1 μm to about 15 μm.

Containers

The containers for the dry solid S-nitrosothiol (for example, S-nitrosoglutathione) or the dry solid pre-composition containing S-nitrosothiol (for example S-nitrosoglutathione), for example as dry solid particles, are preferably oxygen-impermeable and moisture-impermeable. The containers have convenient sizes, particularly unit dosage sizes or sizes in multiples of a unit dose. Those skilled in the art can readily determine appropriate container sizes and the weight of the dry solid S-nitrosothiol (for example, S-nitrosoglutathione) or the dry solid pre-composition containing S-nitrosothiol (for example S-nitrosoglutathione), depending on the intended use and mode of administration. As previously described, it is preferred that the dry solid S-nitrosothiol (for example, S-nitrosoglutathione) or the dry solid pre-composition containing S-nitrosothiol (for example S-nitrosoglutathione) is placed in the container, the container is sealed, and the contents of the container and the inner walls of the container are then sterilised according to the present invention. The container then holds the sterile dry solid S-nitrosothiol (for example, S-nitrosoglutathione) or the sterile dry solid pre-composition containing S-nitrosothiol (for example S-nitrosoglutathione) for storage and transportation until such time as the final pharmaceutical composition is desired to be made up.

The dry solid material can be placed in the containers prior to sterilisation by filling methods known to those skilled in the art. Such containers can be vials, tubes, syringes, ampoules and the like, e.g. for holding powdered formulations, and may be made of any inert material, such as plastics, polymers, glass and the like.

As previously mentioned, because S-nitrosothiols (for example, S-nitrosoglutathione) are light sensitive, they can be stored in suitable overwraps or containers that are impermeable to oxygen and light, for example tinted containers (e.g. amber tinted) or aluminum pouches. Those skilled in the art can readily determine suitable containers, overwraps and the like for storing an S-nitrosothiol and other components useful for maintaining the stability of the S-nitrosothiol. Prior to sealing, the storage system may be treated with at least one inert gas, for example, nitrogen, argon, helium, neon, krypton and xenon, to reduce the oxygen content within the system. The sealed storage system (e.g. amber vials and other light protective storage containers) with the measured dose of S-nitrosothiol may then be subjected to the sterilising treatment in accordance with the present invention. The storage system assists to stabilise the solid formulations and to retain the purity level of the S-nitrosothiol over an extended period of time and normal ambient temperatures.

BRIEF DESCRIPTION OF THE DRAWINGS

The present invention will be described in more detail below, but without limitation, by reference to the accompanying drawings, in which.

EXAMPLES

The following non-limiting examples are provided for further illustration of the present invention.

Example 1

Sterilisation of S-nitrosoglutathione Using E-beam and Gamma Radiation at Unconstrained Temperature Settings S-nitrosoglutathione granule samples from a single manufacturing batch, contained in glass vials (up to 250 mg/vial), were stored before sterilisation surrounded by dry ice (solid $CO_2$) at about −80° C. The matching controls were not irradiated but underwent similar conditions of storage and thermal management before, during and after irradiation, as compared with the S-nitrosoglutathione vials that were irradiated. The control purity levels of the S-nitrosoglutathione, and the level of specific impurities glutathione (GSH) and oxidised glutathione (GSSG) content and total impurities content, were analysed. Vials were exposed to either electron beam (e-beam) irradiations or to gamma irradiations. The vials were removed from the dry ice container and sterilised via two radiation dose conditions (15 kGy and 35 kGy) described below under higher temperature conditions (with surrounding air temperature in the range about 18 to 24° C. and with the temperature of the vials free to fluctuate to higher temperature). After irradiation, the vials were immediately surrounded by dry ice at about −80° C. and analysed for post-sterilisation determination of any changes in purity against the control.

The e-beam radiation was performed using a moving carrier system set up for delivering a 15 kGy dose and a 35 kGy dose. The 15 kGy radiation dose lasted about 10–15 minutes and the temperature reached approximately equal to 27.5° C. (designated ~27.5° C. in the Tables and Figures). The 35 kGy radiation dose lasted about 30 minutes and the temperature reached approximately equal to 27.5° C. (designated ~27.5° C. in the Tables and the Figures). The radiation doses were measured by conventional dosimeters.

The gamma radiation was performed using a moving carrier system set up for delivering a 15 kGy dose and a 35 kGy dose. The 15 kGy dose radiation lasted about 8-10 hours and the temperature reached up to 40° C. The 35 kGy dose radiation lasted about 18-24 hours, with a temperature reaching up to 60° C. The radiation doses received were measured by conventional dosimeters.

Figure 1:
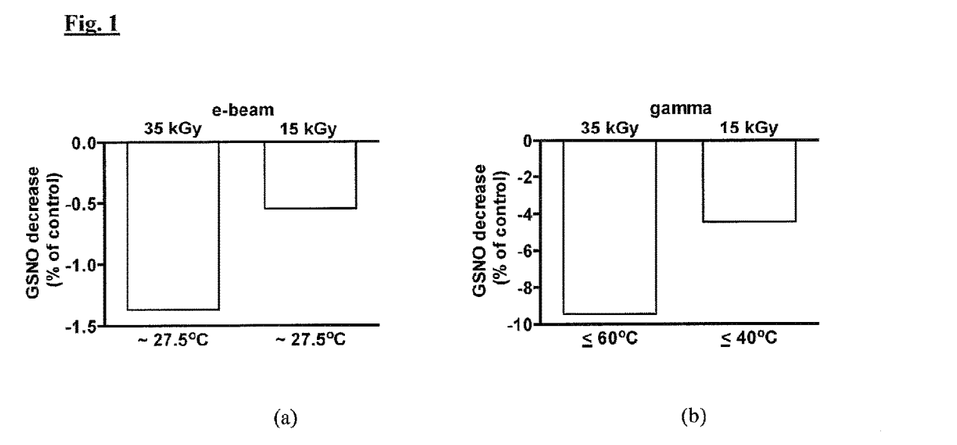
FIG. 1 shows the effects of the (a) e-beam and (b) gamma sterilisation treatment of Example 1 on the purity of the S-nitrosoglutathione (GSNO; % decrease in purity compared with non-irradiated control sample)
Figure 3:
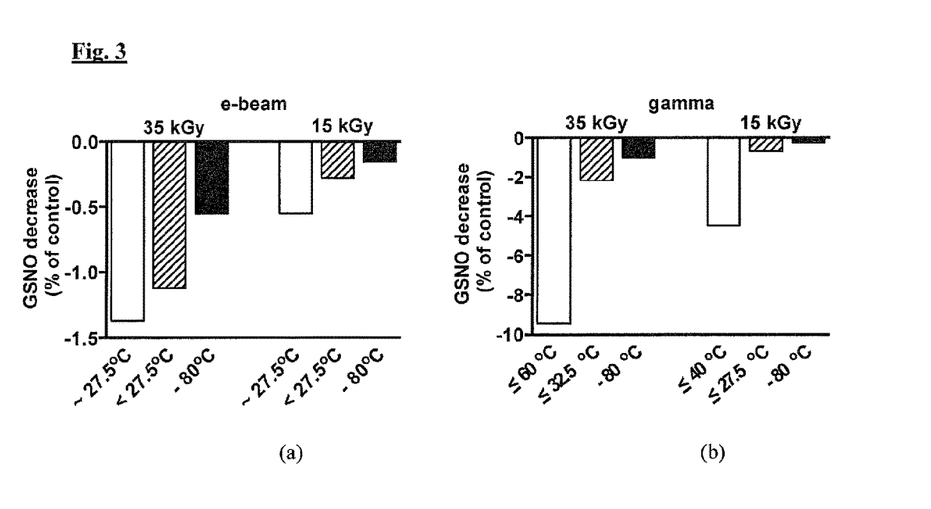
FIG. 3 is a composite of FIGS. 1 and 2 and shows the effects of the (a) e-beam and (b) gamma sterilisation treatments of Examples 1 and 2 on the purity of the S-nitrosoglutathione (GSNO; % decrease in purity compared with non-irradiated control sample; data from Example 1 identified by (1); data from Example 2 identified by (2))

The results are shown in FIGS. 1 and 3 (bars labeled (1) for Example 1) and Table 1.

TABLE 1

Summary of results for e-beam and gamma radiation (Example 1)

| | e-beam | | gamma | |
| --- | --- | --- | --- | --- |
| | | Dose level | | |
| | 35 kGy | 15 kGy | 35 kGy | 15 kGy |
| | | Time of irradiation | | |
| | ~30 minutes | 10-15 minutes | 18-24 hours | 8-10 hours |
| Temperature (° C.) during irradiation | ~27.5 | ~27.5 | ≤60 | ≤40 |
| GSNO purity (decrease % of control) | −1.37 | −0.55 | −9.45 | −4.47 |
| GSH impurity (% unit change) | 0.36 | 0.17 | 0.15 | 0.34 |
| GSSG impurity (% unit change) | 0.32 | 0.11 | 6.63 | 1.25 |
| Total impurities (% unit changes) | 1.26 | 0.53 | 9.12 | 4.25 |

The unconstrained temperature e-beam irradiation of Example 1 at 15 kGy and 35 kGy resulted in a dose dependent decrease in the HPLC purity of S-nitrosoglutathione. The unconstrained temperature gamma irradiation of Example 1 at 15 kGy and 35 kGy resulted in a significant decrease in the HPLC purity of S-nitrosoglutathione dependent to temperature, time and radiation dose level. The use of ionising radiation (e-beam and gamma radiation) at unconstrained temperature leads to degradation of S-nitrosoglutathione as shown by the decrease in purity compared to control. However, the degradation is worse in the case of gamma radiation than in the case of e-beam radiation.

The data show that the level of the specific impurities GSH and GSSG and total impurities increased after e-beam and gamma irradiations in a temperature, time and radiation dose level dependent manner.

Example 2

Sterilisation of S-nitrosoglutathione Using E-beam and Gamma Radiation at Constrained Temperatures The experimental protocol for this Example aims to test in a controlled manner the effects on purity of a sterilizing irradiation temperature (a) at about −80° C. and (b) under positive cooling (with surrounding air temperature in the range about 18 to 24° C. and with the temperature of the vials controlled). The same radiation doses as described for Example 1 were applied.

For this Example, S-nitrosoglutathione granule samples, from the same single manufacturing batch as in Example 1, contained in amber glass vials (100 mg/vial) were stored before sterilisation at about −80° C. The irradiation process at −80° C. was achieved by the presence of dry ice, which was placed to ensure low temperature of the vials but without influencing the radiation dose delivery characteristics. The matching controls were not irradiated but underwent similar conditions of thermal management before, during and after irradiation, as compared with the S-nitrosoglutathione vials that were irradiated.

The method employed for the e-beam arm of this experiment was as follows:

The e-beam radiation was performed using a moving carrier system. The S-nitrosoglutathione vials were stored at −80° C. freezer and transferred to a dry ice container before irradiation. Before the start of irradiation the S-nitrosoglutathione vials destined for irradiation at ambient temperature (and control vials) were removed from the −80° C. freezer and transferred to a location where the surrounding air temperature is controlled at 18° C.

Figure 4:
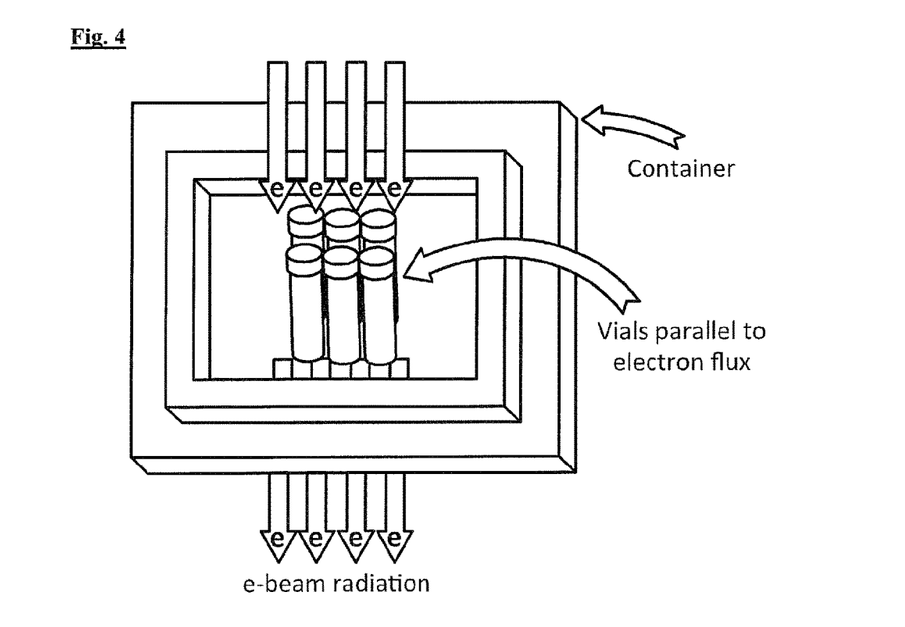
FIG. 4 is a schematic representation of the apparatus for e-beam irradiating vials containing S-nitrosoglutathione (GSNO) in Example 2.

Individual low-temperature containers were used for the vials designated for each target dose and condition of thermal management. A secondary packaging box was placed in the lateral centre at the bottom of the first low-temperature container, with the vials oriented upright. The position of each vial in the configuration was documented. The vials were always irradiated from the same side. FIG. 4 shows a possible arrangement of vials in a container for e-beam irradiation. The arrows marked "e" show the direction of the radiation. For the S-nitrosoglutathione vials requiring cold chain management, dry ice was placed at each lateral short side of the container to ensure a cold chain was maintained during the irradiation process. Each container was placed in an irradiation container.

Both the 15 kGy e-beam and 35 kGy radiation doses lasted a few seconds.

Following completion of the desired irradiation process, the irradiated S-nitrosoglutathione containing vials and correspondent controls were stored at −80° C. in a freezer for subsequent analysis.

The method employed for the gamma arm of this experiment was as follows:

The gamma radiation was performed using gamma radiation emitted from cobalt-60 radioactive sources. The S-nitrosoglutathione vials were stored at −80° C. in a freezer and transferred to a dry ice container before irradiation. Before the start of irradiation, the S-nitrosoglutathione vials destined for irradiation at ambient temperature (and control vials) were removed from the −80° C. freezer and transferred to a location where the surrounding temperature was controlled at 18° C.

Individual low-temperature containers were used for the samples designated for each target dose and condition of thermal management, as described above in relation to the e-beam arm of this Example.

Figure 5:
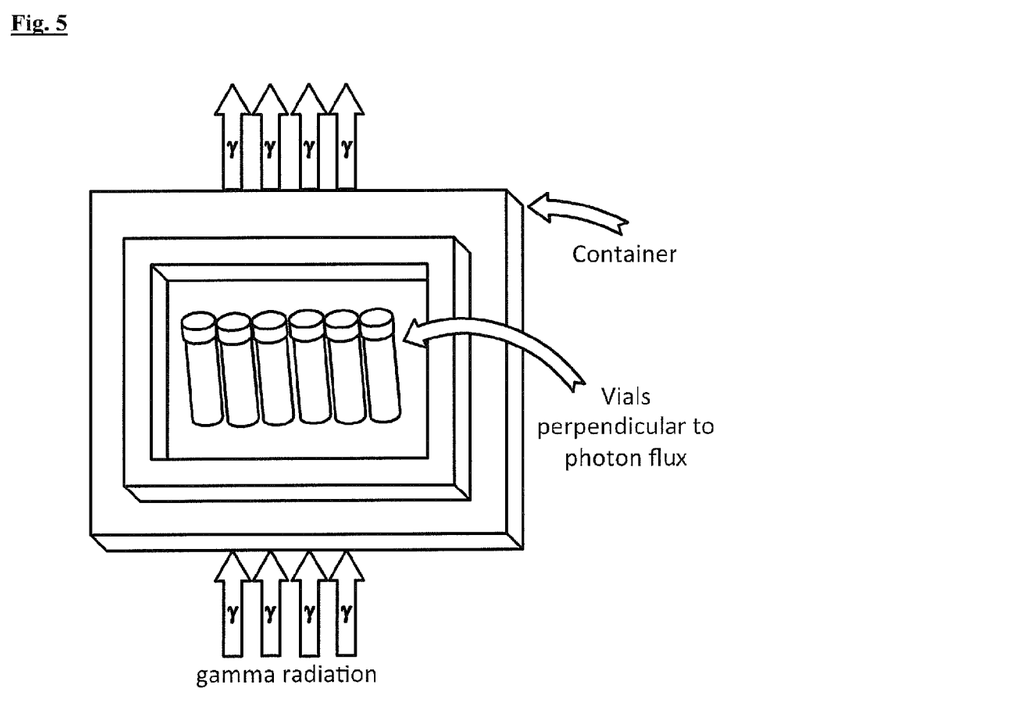
FIG. 5 is a schematic representation of the apparatus for gamma irradiating vials containing S-nitrosoglutathione (GSNO) in Example 2.

The secondary packaging was placed in the lateral centre at the bottom of first low-temperature container, with the vials oriented upright. FIG. 5 shows a possible arrangement of vials in a container for gamma irradiation. The arrows marked "γ" show the direction of the radiation. For the S-nitrosoglutathione product requiring cold chain management, dry ice was placed at each lateral short side of the low-temperature container to ensure a cold chain was maintained during the irradiation process.

Each low-temperature container was placed in the lateral centre of an irradiation container.

The 15 kGy radiation dose lasted 2 hours and 8 minutes whereas the 35 kGy dose lasted about 5 hours and 8 minutes.

When necessary, the dry ice was replenished before execution of the second irradiation.

Following completion of the irradiation process, the irradiated S-nitrosoglutathione products were placed in the designated −80° C. freezer. The control samples were moved from the 18° C. controlled location to the designated −80° C. freezer upon completion of the second irradiation. The time of transfer was recorded.

Figure 2:
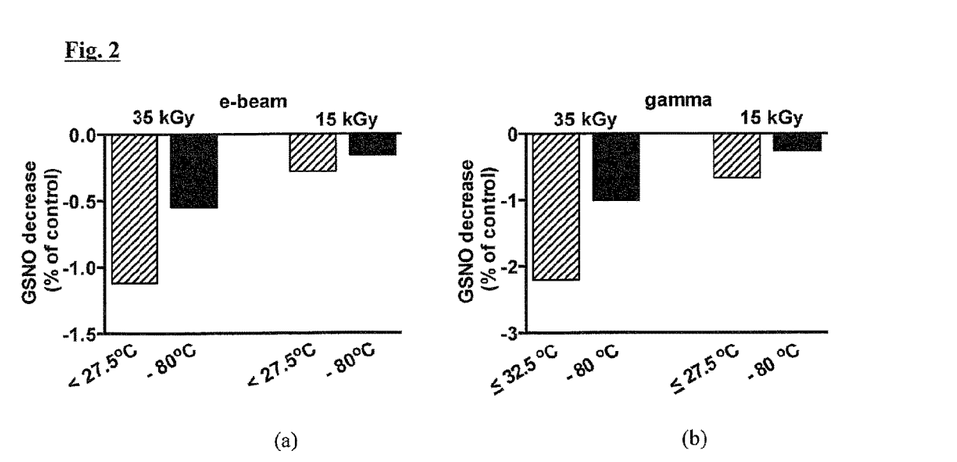
FIG. 2 shows the effects of the (a) e-beam and (b) gamma sterilisation treatment of Example 2 on the purity of the S-nitrosoglutathione (GSNO; % decrease in purity compared with non-irradiated control sample)

The results are shown in FIG. 2 and FIG. 3 (labeled (2) for Example 2), and Table 2.

TABLE 2

Summary of results for e-beam and gamma radiation (Example 2)

| | e-beam | | | | gamma | | | |
|---|---|---|---|---|---|---|---|---|
| Dose level | 35 kGy | | 15 kGy | | 35 kGy | | 15 kGy | |
| Time of irradiation | Few sec. | | Few sec. | | ~5 h | | ~2 h | |
| Temperature (° C.) during irradiation | <27.5 | −80 | <27.5 | −80 | ≤32.5 | −80 | ≤27.5 | −80 |
| GSNO purity (decrease % of control) | −1.12 | −0.55 | −0.28 | −0.16 | −2.2 | −1.01 | −0.67 | −0.26 |
| GSH impurity (% unit change) | 0.29 | 0.23 | 0.13 | 0.10 | 0.43 | 0.29 | 0.17 | 0.11 |
| GSSH impurity (% unit change) | 0.23 | 0.07 | 0.13 | 0.10 | 0.36 | 0.36 | 0.14 | 0.11 |
| Total impurities (% unit changes) | 1.08 | 0.54 | 0.27 | 0.16 | 2.11 | 0.96 | 0.63 | 0.25 |

The e-beam irradiations of Example 2 at 15 kGy and 35 kGy resulted in a small, temperature, time and dose level dependent decrease in the HPLC purity of S-nitrosoglutathione (GSNO); FIGS. 2 and 3 (labeled (2) for Example 2) and Table 2.

The gamma irradiations of Example 2 at 15 kGy and 35 kGy resulted in a small, temperature, time and dose level dependent decrease in the HPLC purity of S-nitrosoglutathione (GSNO); FIGS. 2 and 3 labeled (2) for Example 2) and Table 6.

In all the irradiations of Example 2, the level of specific impurity GSH and GSSG and total impurities increased in a small temperature, time and dose level dependent manner, after e-beam and gamma radiation Table 2.

Discussion

The results of Examples 1 and 2 are summarized in Tables 3 and 4:

TABLE 3

Summary of results for e-beam radiation
[(1) = Example 1; (2) = Example 2]

| Conditions | Example 1 | Example 2 | | Example 1 | Example 2 | |
|---|---|---|---|---|---|---|
| Dose level | 35 kGy | | | 15 kGy | | |
| Vial type | Clear | Amber | | Clear | Amber | |
| Time of irradiation | ~30 minutes | Few seconds | | 10-15 minutes | Few seconds | |
| Temperature (° C.) during irradiation | ~27.5 | −80 | <27.5 | ~27.5 | −80 | <27.5 |
| GSNO purity (decrease % of control) | −1.37 | −0.55 | −1.12 | −0.55 | −0.16 | −0.28 |

TABLE 4

Summary of results for gamma radiation
[(1) = Example 1; (2) = Example 2]

| Conditions | Example 1 | Example 2 | | Example 1 | Example 2 | |
|---|---|---|---|---|---|---|
| Dose level | 35 kGy | | | 15 kGy | | |
| Vial type | Clear | Amber | | Clear | Amber | |
| Time of irradiation (hours) | 18-24 | ~5 | | 8-10 | ~2 | |
| Temperature (° C.) during irradiation | ≤60 | −80 | ≤32.5 | ≤40 | −80 | ≤27.5 |
| GSNO purity (decrease % of control) | −9.45 | −1.01 | −2.2 | −4.47 | −0.26 | −0.67 |

The above results show that optimised specific conditions exist to sterilise pharmaceutical S-nitrosothiols such as, for example, S-nitrosoglutathione. The decomposition of S-nitrosoglutathione in vials was examined following irradiation (by e-beam and gamma) at two dose levels (15 kGy and 35 kGy) using different conditions (different vials, different duration and temperature of irradiation) in two different experiments. These studies confirm that ionising radiation can decompose S-nitrosoglutathione; however they demonstrate, for the first time, that specific conditions of temperature and irradiation time and dose can minimise its decomposition, enabling the fulfilment of pharmaceutical regulatory requirements. E-beam radiation appears to decompose S-nitrosoglutathione less than gamma radiation at a parity of dosage. Decomposition is minimised by lowering the temperature and shortening the duration of the irradiation.

The foregoing broadly describes the present invention without limitation. Variations and modifications as will be readily apparent to those skilled in the art are intended to be covered. The scope of protection of the present invention shall be determined by reference to the appended claims as properly construed according to law.

REFERENCES

The literature references in the foregoing description of the invention are as follows:

Ahn D U, Lee E J (2002). Production of off-odor volatiles from liposome-containing aminoacid homopolymers by irradiation. *J Food Sci* 67: 7.

Al-Sa'doni H, Ferro A (2000). S-Nitrosothiols: a class of nitric oxide-donor drugs. *Clin Sci (Lond)* 98: 507-520.

Butler A R, Rhodes P (1997). Chemistry, analysis, and biological roles of S-nitrosothiols. *Anal Biochem* 249: 1-9.

Hart T W (1985). *Tetrahedron Letters,* 26(16), 1985, 2013 to 2016.

Keaney J F, Jr., Simon D I, Stamler J S, Jaraki O, Scharfstein J, Vita J A, et al. (1993). NO forms an adduct with serum albumin that has endothelium-derived relaxing factor-like properties. *J Clin Invest* 91: 1582-1589.

Lin C-E, Garvey D S (2005). Identification of the nitrate produced from gamma-radiation sterilization of S-Nitrosoglutathione. Abstract ANYL174, General Papers 1.00 pm to 9.00 pm, 28 Aug. 2005, Hall A Poster, 230$^{th}$ ACS Meeting, Washington D.C., 28 Aug.- 1 Sep. 2005.

Looker D, Beyer W (2008). WO 2008/153762 A2 S-nitrosothiol formulations and storage systems.

Manoj V M, Aravind Usha K, Aravindakumar C T (2009). Decomposition of S-Nitrosothiols Induced by UV and Sunlight. *Advances in Physical Chemistry* 2009: 6.

Parent M, Dahboul F, Schneider R, Clarot I, Maincent P, Leroy P, et al. (2013). A Complete Physicochemical Identity Card of S-nitrosoglutathione. *Current Pharmaceutical Analysis* 9: 12.

Radomski M W, Rees D D, Dutra A, Moncada S (1992). S-nitroso-glutathione inhibits platelet activation in vitro and in vivo. *Br J Pharmacol* 107: 745-749.

Rees D D, Palmer R M, Moncada S (1989a). Role of endothelium-derived nitric oxide in the regulation of blood pressure. *Proc Natl Acad Sci USA* 86: 3375-3378.

Rees D D, Higgs A, Moncada S (2001). Nitric Oxide and the Vessel Wall. In: Wilkins L W (ed). *Hemostasis and Thrombosis*, edn. p^pp 10.

Rees D D, Palmer R M, Hodson H F, Moncada S (1989b). A specific inhibitor of nitric oxide formation from L-arginine attenuates endothelium-dependent relaxation. *Br J Pharmacol* 96: 418-424.

Singh R J, Hogg N, Joseph J, Kalyanaraman B (1995). Photosensitized decomposition of S-nitrosothiols and 2-methyl-2-nitrosopropane. Possible use for site-directed nitric oxide production. *FEBS Lett* 360: 47-51.

Singh R J, Hogg N, Joseph J, Kalyanaraman B (1996a). Mechanism of nitric oxide release from S-nitrosothiols. *J Biol Chem* 271: 18596-18603.

Singh S P, Wishnok J S, Keshive M, Deen W M, Tannenbaum S R (1996b). The chemistry of the S-nitrosoglutathione/glutathione system. *Proc Natl Acad Sci USA* 93: 14428-14433.

Stamler J S, Toone E J (2002). The decomposition of thionitrites. *Current opinion in chemical biology* 6: 779-785.

Stamler J S, Jaraki O, Osborne J, Simon D I, Keaney J, Vita J, et al. (1992). Nitric oxide circulates in mammalian plasma primarily as an S-nitroso adduct of serum albumin. *Proc Natl Acad Sci USA* 89: 7674-7677.

The invention claimed is:

1. A method of preparing sterile dry solid S-nitrosothiol or a sterile dry solid pharmaceutical pre-composition comprising S-nitrosothiol, said method comprising:

exposing dry solid S-nitrosothiol or a dry solid pharmaceutical pre-composition comprising S-nitrosothiol to a sterilising dose of ionising radiation in an environment sealed from external contamination to yield a sterile product of said sterile dry solid S-nitrosothiol or sterile dry solid pharmaceutical pre-composition comprising S-nitrosothiol, wherein said sterile product has an S-nitrosothiol purity of at least about 95% and a sterility assurance level (SAL) of $10^{-6}$ or lower.

2. A method as claimed in claim 1, wherein the ionising radiation is selected from electron beam (e-beam) radiation, gamma radiation and X-rays.

3. A method as claimed in claim 1, wherein the exposure to the ionising radiation is performed under conditions such that there is no reduction of the purity of the S-nitrosothiol or that its purity is reduced by not more than about 2.0%, through degradation.

4. A method as claimed in claim 1, wherein the dry solid S-nitrosothiol or dry solid pharmaceutical pre-composition comprising S-nitrosothiol is maintained at a temperature not greater than about 40° C. during the sterilising exposure to the ionising radiation.

5. A method as claimed in claim 1, wherein an absorbed dose of ionising radiation up to about 50 kGy is used to sterilise the dry solid S-nitrosothiol or dry solid pharmaceutical pre-composition comprising S-nitrosothiol and
  (a) electron beam (e-beam) radiation is used for an exposure time which is less than about 1 hour; or
  (b) gamma radiation is used for an exposure time which is less than about 24 hours.

6. A method as claimed in claim 1, wherein:
  (a) the ionising radiation is electron beam (e-beam) radiation and the dry solid S-nitrosothiol or dry solid pharmaceutical pre-composition comprising S-nitrosothiol is maintained during the sterilising exposure to the ionising radiation at a temperature not greater than about 35° C.; or
  (b) the ionising radiation is gamma radiation and the dry solid S-nitrosothiol or dry solid pharmaceutical pre-composition comprising S-nitrosothiol is maintained during the sterilising exposure to the ionising radiation at not a temperature greater than about 35° C.

7. A method as claimed in claim 1, wherein the ionising radiation is electron beam radiation at an absorbed dose of up to about 50 kGy, the dry solid S-nitrosothiol or a dry solid pharmaceutical pre-composition comprising S-nitrosothiol to be sterilised has a starting temperature at room temperature conditions with freedom to fluctuate higher during said exposing, and the exposure to e-beam radiation taking place over up to about 1 hour.

8. A method as claimed in claim 1, wherein the ionising radiation is electron beam radiation at an absorbed dose of up to about 50 kGy, the dry solid S-nitrosothiol or a dry solid pharmaceutical pre-composition comprising S-nitrosothiol to be sterilised is maintained at a temperature below about 35° C., and the exposure to the radiation taking place over up to about 1 hour.

9. A method as claimed in claim 1, wherein the ionising radiation is gamma radiation at an absorbed dose of up to about 50 kGy, the dry solid S-nitrosothiol or a dry solid pharmaceutical pre-composition comprising S-nitrosothiol to be sterilised is maintained at a temperature below about 35° C., and the exposure to the radiation taking place over up to about 24 hours.

10. A method as claimed in claim 1, wherein the environment sealed from external contamination is in a dry sealed container in which the dry solid S-nitrosothiol or a dry solid pharmaceutical pre-composition comprising S-nitrosothiol is contained prior to said exposing.

11. A method as claimed in claim 10, wherein the environment after said exposing is a dry sterile environment within the sealed container.

12. A method as claimed in claim 10, wherein the container has walls that are tinted or opaque to light.

13. A method as claimed in claim 10, wherein the container is oxygen-impermeable and moisture-impermeable.

14. A method as claimed in claim 1, wherein prior to said exposing, said method further comprising:
  placing said dry solid S-nitrosothiol or a dry solid pharmaceutical pre-composition comprising S-nitrosothiol into a dry container; and
  sealing said container to yield said environment sealed from external contamination.

15. A method as claimed in claim 14, wherein after said exposing said container holds said sterile product for storage and transportation until used for a final pharmaceutical composition for therapeutic or prophylactic use.

* * * * *